US011158426B1

(12) United States Patent
Lo

(10) Patent No.: US 11,158,426 B1
(45) Date of Patent: Oct. 26, 2021

(54) WEARABLE DEVICE TRACKING A BIOMARKER IN A TEAM FOR EARLY INDICATION OF INFECTIOUS DISEASE

(71) Applicant: Elysian Labs, Inc, Oakland, CA (US)

(72) Inventor: Joanne Chung-Yan Lo, Oakland, CA (US)

(73) Assignee: Elysian Labs, Incn, Berkeley, CA (US)

( * ) Notice: Subject to any disclaimer, the term of this patent is extended or adjusted under 35 U.S.C. 154(b) by 0 days.

(21) Appl. No.: 16/884,043

(22) Filed: May 27, 2020

Related U.S. Application Data

(60) Provisional application No. 63/004,391, filed on Apr. 2, 2020.

(51) Int. Cl.
*G16H 50/20* (2018.01)
*G06N 3/08* (2006.01)
*G06F 1/16* (2006.01)

(52) U.S. Cl.
CPC ............. *G16H 50/20* (2018.01); *G06F 1/163* (2013.01); *G06N 3/08* (2013.01)

(58) Field of Classification Search
None
See application file for complete search history.

(56) References Cited

U.S. PATENT DOCUMENTS

2006/0149597 A1* 7/2006 Powell .................. G06Q 10/10 705/2

OTHER PUBLICATIONS

Paradiso, Rita. "Wearable health care system for vital signs monitoring." 4th International IEEE EMBS Special Topic Conference on Information Technology Applications in Biomedicine, 2003 . . . IEEE, 2003.*
Kroll, Ryan R., et al. "Use of wearable devices for post-discharge monitoring of ICU patients: a feasibility study." Journal of intensive care 5.1 (2017): 64.*
World Health Organization. "Managing epidemics: key facts about major deadly disease." 260 pages, 2018.*
Lu, Yinying, et al. "Chinese military medical teams in the Ebola outbreak of Sierra Leone." BMJ Military Health 162.3 (2016): 198-202.*
Amendola, S., et al. "Design, calibration and experimentation of an epidermal RFID sensor for remote temperature monitoring." IEEE Sensors Journal 16.19 (2016): 7250-7257.*
Sun, Guanghao, et al. "KAZEKAMO: An infection screening system remote monitoring of multiple vital-signs for prevention of pandemic diseases." 2014 IEEE 3rd Global Conference on Consumer Electronics (GCCE). IEEE, 2014.*
Tello, Juan Pablo, et al. "Remote monitoring system of ECG and human body temperature signals." IEEE Latin America Transactions 11.1 (2013): 314-318.*
Noury, N., et al. "VTAMN—A smart clothe for ambulatory remote monitoring of physiological parameters and activity." The 26th Annual International Conference of the IEEE Engineering in Medicine and Biology Society. vol. 2. IEEE, 2004.*

* cited by examiner

*Primary Examiner* — G Steven Vanni

(57) ABSTRACT

A method for addressing tactical situations via tactical devices may include (i) identifying at least one wearable device that monitors at least one biomarker of a user wearing the at least one wearable device during a span of time while carrying out daily activities, (ii) receiving, by a server, information about activity of the at least one biomarker monitored by the at least one wearable device during the span of time, (iii) determining that the activity of the at least one biomarker during the span of time includes an early indication of an illness, and (iv) transmitting an alert about the early indication of the illness detected by the at least one wearable device. Various other systems, and methods are also disclosed.

20 Claims, 7 Drawing Sheets

WEARABLE DEVICE TRACKING A BIOMARKER IN A TEAM FOR EARLY INDICATION OF INFECTIOUS DISEASE

CROSS REFERENCE TO RELATED APPLICATIONS

This application claims the benefit of U.S. Provisional Application No. 63/004,391, filed 2 Apr. 2020, the disclosure of which is incorporated, in its entirety, by this reference.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
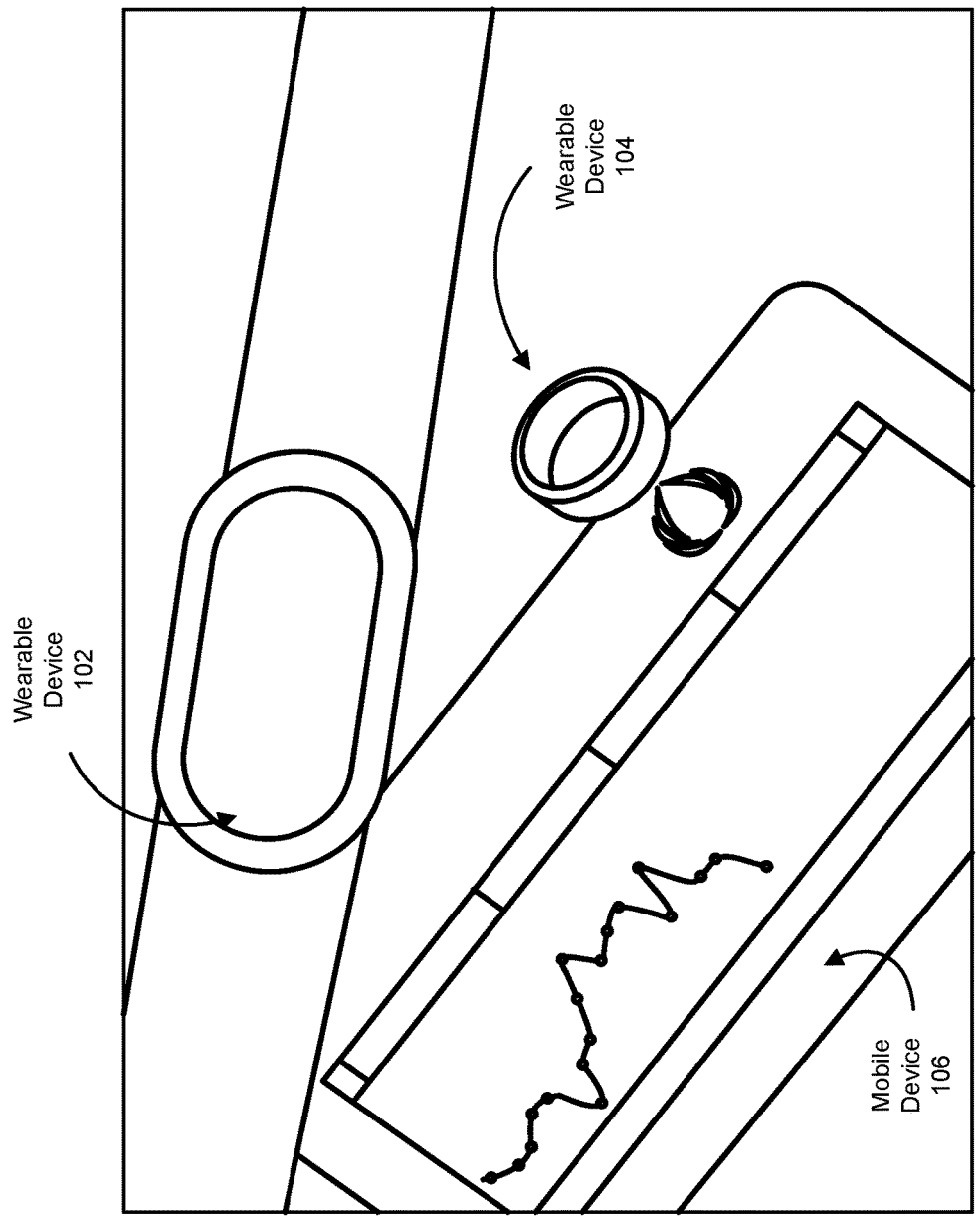
FIG. 1 is an illustration of example wearable devices and an example mobile device.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

The present disclosure is generally directed to systems and methods for detecting early indications of illness via biomarker data from wearable devices. As will be explained in greater detail below, by collecting biomarker data from wearable devices and then analyzing the data for early indications of illness, the systems described herein may identify the onset of an illness before obvious symptoms (e.g., coughing, sneezing, high fever, etc.) become apparent. Identifying an illness early may help the user seek treatment earlier as well as prevent the user from infecting additional people, improving health outcomes for entire communities. By automatically collecting biomarker data via wearable devices that the user wears while performing everyday activities, the systems described herein may track biomarkers without interfering with a user's life and without gaps in data caused by users forgetting to collect data manually (e.g., via a thermometer or other non-wearable device). Additionally, the systems and methods described herein may improve the functioning of a computing device that analyzes biomarker data by providing the computing device with consistent, high-quality biomarker data. As discussed in greater detail below, the various embodiments disclosed herein, whether used alone or in combination, may improve the field of healthcare by identifying early indications of illnesses, leading to more proactive treatment and decreased community transmission.

In some embodiments, the systems described herein may include a mobile application that collects data from wearable devices. FIG. 1 is an illustration of an example set of wearable devices that send data to a mobile device. The term "wearable device," as used herein, may generally refer to any wireless device designed to be worn during everyday activity (as opposed to, e.g., medical devices designed to be worn while conducting tests) that is capable of detecting, storing, and/or transmitting data about one or more biomarkers. In some embodiments, a wearable device may include a general-purpose smart device, such as a smartwatch, that has functions unrelated to biomarker data. Additionally or alternatively, a wearable device may include a purpose-built wearable device that primarily has functions related to biomarker data, such as a chest strap for monitoring breathing and/or heart activity during exercise. In some examples, a wearable device may be an exercise monitor, sleep monitor, and/or other type of non-prescribed and/or commercial off-the-shelf monitor. In some embodiments, a wearable device may be produced by a third-party vendor that does not produce the systems described herein. Examples of form factors for wearable devices may include, without limitation, watches, bracelets, armbands, rings, chest straps, thigh straps, anklets, forehead straps, hats, necklaces, belts, shirts, pants, shoes, and/or gloves. Examples of wearable devices may include, without limitation, OURA rings, POLAR VANTAGE watches, POLAR chest straps, APPLE watches, GARMIN heart rate monitors, and/or BODIMETRICS CIRCUL rings. In some embodiments, the systems described herein may use data from wearable devices produced by multiple different third-party vendors. For example, the systems described herein may retrieve breathing data and/or heart rate data from a POLAR chest strap, sleep data and/or heart rate data from an OURA ring, and heart rate data from an APPLE watch. In another example, the systems described herein may retrieve data from a smart watch and a ring, from a chest strap and a smart watch, or from a chest strap and a ring.

In one embodiment, a wearable device 102 may include a chest strap that monitors biomarkers such as heart rate. Additionally or alternatively, a wearable device 104 may include a ring that monitors biomarkers such as sleep quality, heart rate, and/or temperature. In one example, wearable device 102 and/or wearable device 104 may send data to a mobile device 106 that is configured with a biomarker monitoring application. In some embodiments, wearable device 102 and wearable device 104 may both send data directly to the biomarker monitoring application. Additionally or alternatively, wearable device 102 and/or wearable device 104 may each send data to device-specific applications and the biomarker monitoring application may collect the data from the device-specific applications. The term "biomarker," as used herein, generally refers to any measurable, variable aspect of a person's physiology. In some examples, a biomarker and/or a change in a biomarker may be indicative of an illness. Examples of biomarkers may include, without limitation, heart rate, heart rate variability, temperature, sleep duration, sleep disruption, levels of various chemicals, proteins, and/or cells (e.g., white blood cells, hormones, etc.), and/or breathing patterns.

In some examples, a user may wear one or more wearable devices while performing everyday activities. The term "everyday activities" or "daily activities," as used herein, generally refers to activities that are part of a user's typical day, professional duties, and/or routine, as opposed to activities specifically organized to collect data. For example, going for a jog outside or on a treadmill at the gym may be a daily activity for a user while going for a jog on a hospital treadmill while monitored by medical devices may not be a daily activity. In another example, performing physical training may be a daily activity for a member of the military. Similarly, lifting a heavy patient onto a stretcher may be a daily activity for a paramedic. Sleeping, eating, walking, exercising, and/or performing professional duties may all be examples of daily activities. In some embodiments, a user may wear wearable devices continuously for one or more days. In one example, a user may wear every wearable device in a set of wearable devices (e.g., a watch, chest strap, and/or ring) continuously. In another example, a user may wear a set of wearable devices continuously by wearing some wearable devices during some spans of time (e.g., a watch while awake) and other wearable devices during other spans of time (e.g., a sleep tracking ring during sleep) such that continuous data collection by the wearable devices as a set is possible.

Figure 2:
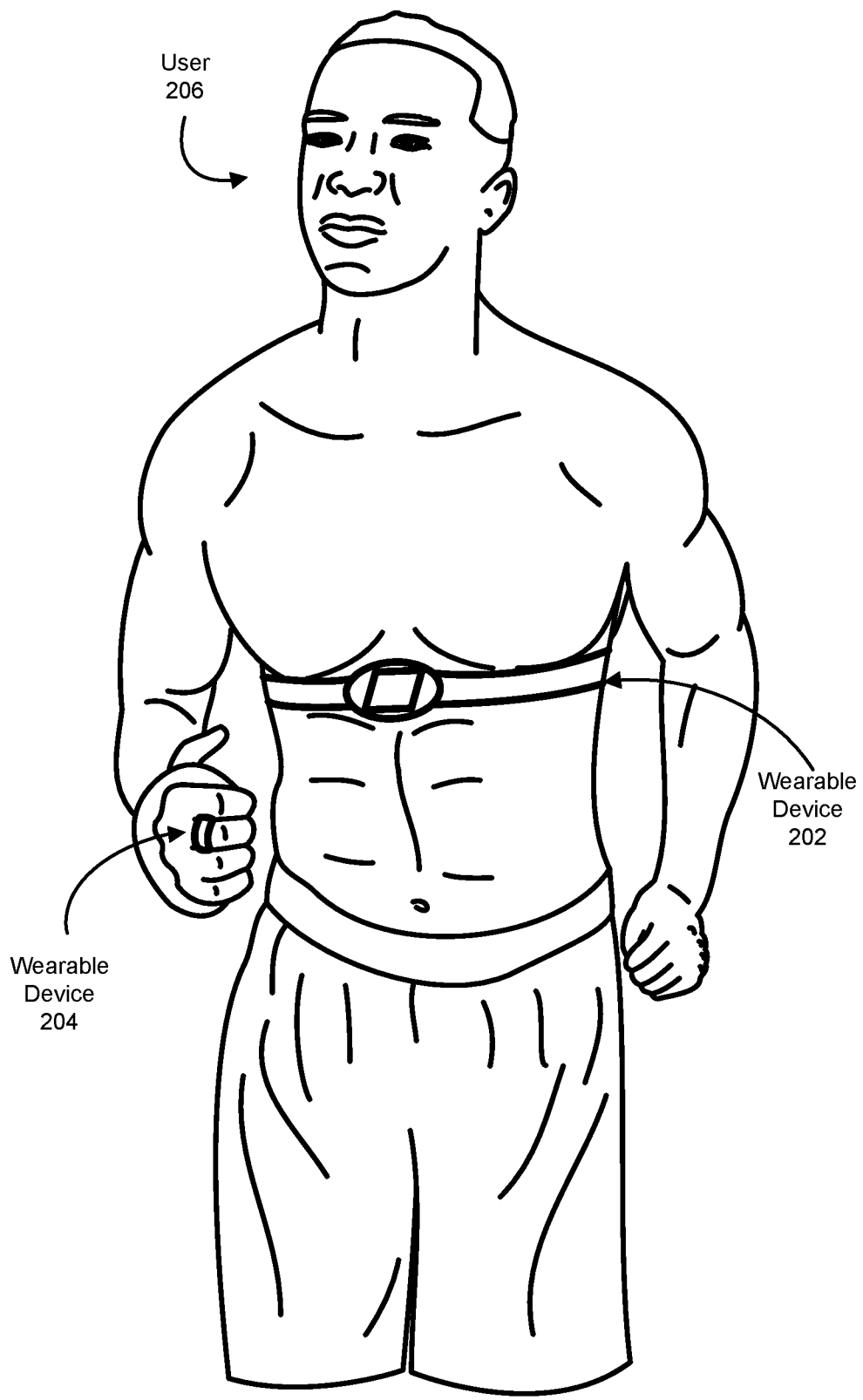
FIG. 2 is an illustration of an example user wearing wearable devices while performing daily activities.

In one example, as illustrated in FIG. 2, a user 206 may wear a wearable device 202 and/or a wearable device 204 while exercising. In some examples, wearable device 202 may be a chest strap that monitors heart rate and/or wearable device 204 may be a ring that monitors temperature, heart rate, blood oxygen saturation, and/or other biomarkers. In some embodiments, a wearable device such as a ring or watch may capture photoplethysmographic (PPG) signals and/or may use PPG signals to determine heart rate and/or heart rate variability. In one embodiment, the systems described herein may use 3-axis accelerometry (e.g., as recorded by the accelerometer of a wearable device such as wearable device 202 and/or 204) to determine movement. In some examples, the systems described herein may track daytime and/or nighttime body temperature via a negative temperature coefficient sensor in a wearable device such as a ring and/or watch. In one embodiment, the systems described herein may monitor biomarker activity over time. For example, the systems described herein may establish a baseline of the user's baroreflex and/or other pressure-related mechanism of the heart with a wearable device such as wearable device 202. In one example, the systems described herein may compare the heart rate of user 206 (e.g., as recorded by wearable device 202) while exercising to previously recorded heart rates to determine if the current heart rate is higher than is typical for this type of activity (e.g., aerobic exercise). In one example, the systems described herein may monitor the heart rate of user 206 after exercise to measure when the heart rate returns to resting.

In some examples, changes in heart rate compared to normal during exercise and/or during recovery and/or changes in recovery time may be an early indication of an illness. The term "early indication," as used herein, generally refers to changes in biomarkers that take place before the onset of the more readily identifiable symptoms of an illness. For example, a change in heart rate variability may be an early indication while a high fever may be a readily identifiable symptom. In another example, sleep disruption may be an early indication while a persistent cough may be a readily identifiable symptom. In some examples, an early indication of an illness may be a combination of changes to biomarkers. For example, coronavirus disease 2019 (COVID-19) infections have a distinctive pattern in the inflammatory response caused in the patient's overall system, lungs, and heart. In one example, the systems described herein may detect the changes that this inflammatory response causes in heart rate and/or heart rate variability as early indications of a COVID-19 infection.

Figure 3:
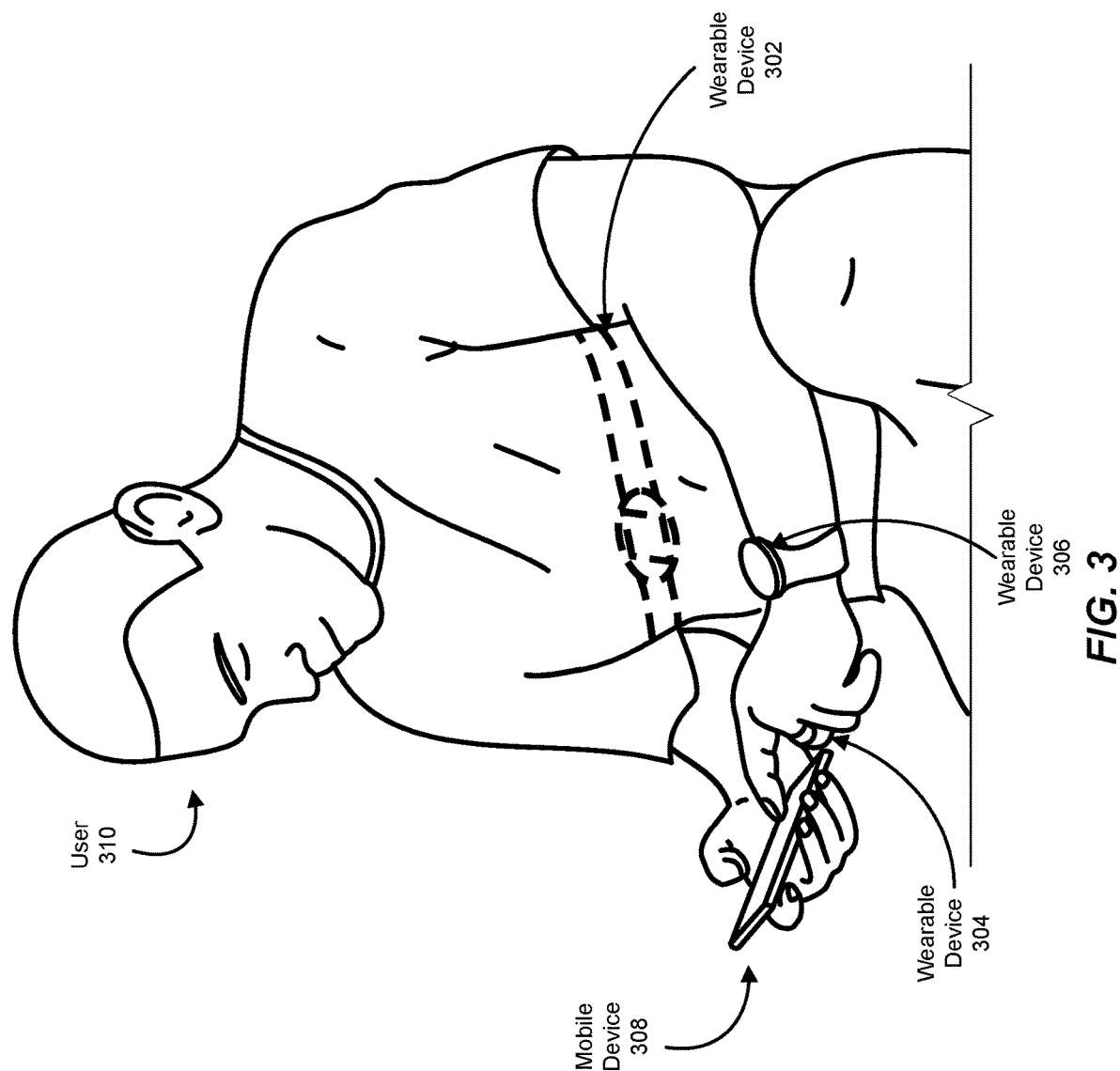
FIG. 3 is an illustration of an example user interacting with a mobile device.

In some embodiments, the systems described herein may surface biomarker and/or illness indication data to a user via a mobile device. For example, as illustrated in FIG. 3, a user 310 may wear multiple wearable devices, such as wearable devices 302, 304, and/or 306, that may send biomarker data to a mobile device 308. In some embodiments, user 310 may view biomarker data and/or any detected indications of illness via an app on mobile device 308. Although illustrated as a mobile phone, mobile device 308 may represent any suitable mobile device. Additionally or alternatively, user 310 may view data collected and/or produced by the systems described herein on a smart wearable device, such as wearable device 306. In some examples, user 310 may view data collected and/or produced by the systems described herein on a computing device, such as a laptop or desktop computer. In some embodiments, the systems described herein may enable user 310 to configure settings for monitoring and/or alerts. For example, mobile device 308 may receive input from user 310 specifying a specific illness for which to monitor for early indications. Additionally or alternatively, mobile device 308 may receive input from user 310 specifying additional devices to which to send alerts if early indications of an illness are detected. In some embodiments, the systems described herein may send an alert that includes a recommended action or actions for the user based on the probability that the user is ill and/or the type of illness. For example, if the systems described herein determine that the user has a greater than 50% chance of being infected with COVID-19, the systems described herein may send an alert that prompts the user to self-isolate for two weeks. In some embodiments, mobile device 308 may prompt user 310 to manually enter health information and/or other information. For example, mobile device 308 may prompt user 310 to fill out a daily health survey. In some embodiments, mobile device 308 may prompt a user to fill out a survey in response to detecting potential early indications of an illness.

Figure 4:
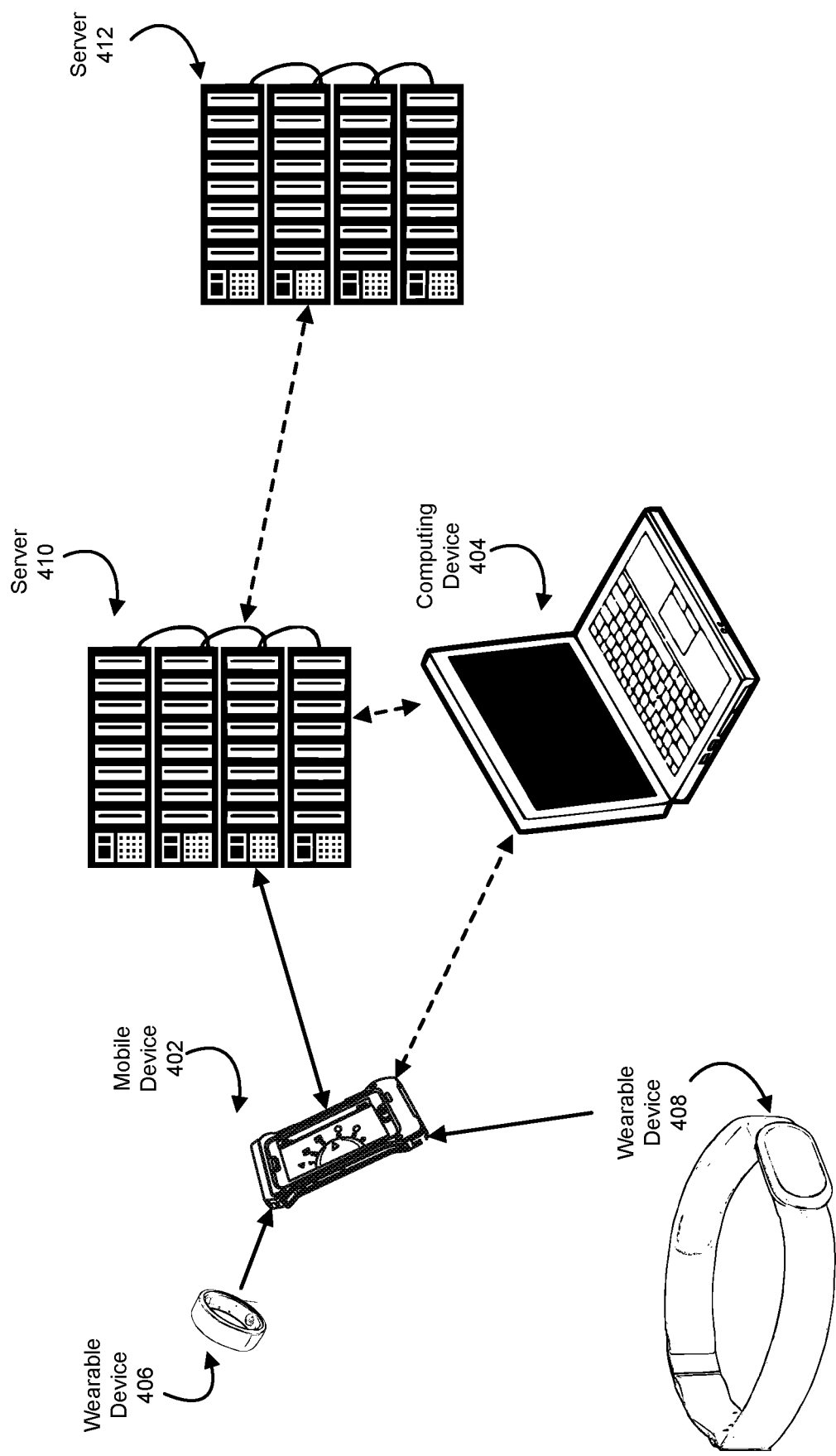
FIG. 4 is diagram of an example system for detecting early indications of illnesses.

In some embodiments, the systems described herein may send data to one or more servers for processing. For example, as illustrated in FIG. 4, a mobile device 402 may receive biomarker data from wearable devices 406 and/or 408 and may send that data to a server 410 for processing and/or analysis. In one embodiment, server 410 may clean, format, and/or otherwise pre-process the data before sending the data to a server 412 that analyzes the processed biomarker data for early indications of illness. In one example, server 412 may be a specialized medical server operated by a third party, such as a medical institution. In other embodiments, server 410 may both process and analyze the data. In some embodiments, the systems described herein may rate different types of data from different types of wearable devices at a different level of reliability. For example, the systems described herein may rate sleep disruption data from a chest strap such as wearable device 408 lower than sleep disruption data from a ring such as wearable device 406. In another example, the systems described herein may rate heart rate data from a chest strap and a ring as equally reliable. In one embodiment, server 410 may process the biomarker data by discarding and/or assigning a lower weighting to data collected by wearable devices with a lower reliability rating.

In some embodiments, a computing device 404 may receive data from mobile device 402 and/or server 410. Although illustrated as a laptop, computing device 404 may generally represent any type of personal computing device and/or mobile device. In some examples, computing device 404 may be operated by a team leader of a team that includes the operator of mobile device 402. For example, a squad leader of a military squad, a team leader of a team of paramedics, and/or any other suitable type of team leader. In one embodiment, the systems described herein may transmit an alert to computing device 404 in response to detecting an early indication of an illness in any team member. In some embodiments, the systems described herein may receive input from computing device 404 specifying what illness or type of illness (e.g., the cold, the flu, COVID-19, etc.) to detect early indications of. In some examples, computing device 404 may display biomarkers and/or other relevant data collected by wearable devices of team members to enable the team leader to make decisions about the team members (e.g., whether to send a team member to work or to get medical attention). In one embodiment, the systems described herein may correlate team members with team leaders by displaying a key (e.g., a numeric key) on team member devices that, when entered into a team leader device, registers the team member device as part of the team. In some embodiments, a team leader device may be a device that is configured with a setting identifying the device as a team leader device and/or a device that is associated with a team leader account (e.g., an account that has permission to view data for other user accounts). In some embodiments, a team leader device and/or a team leader account may have special settings, permissions, and/or hardware and/or software configurations that are not present in normal user devices and/or accounts.

Figure 5:
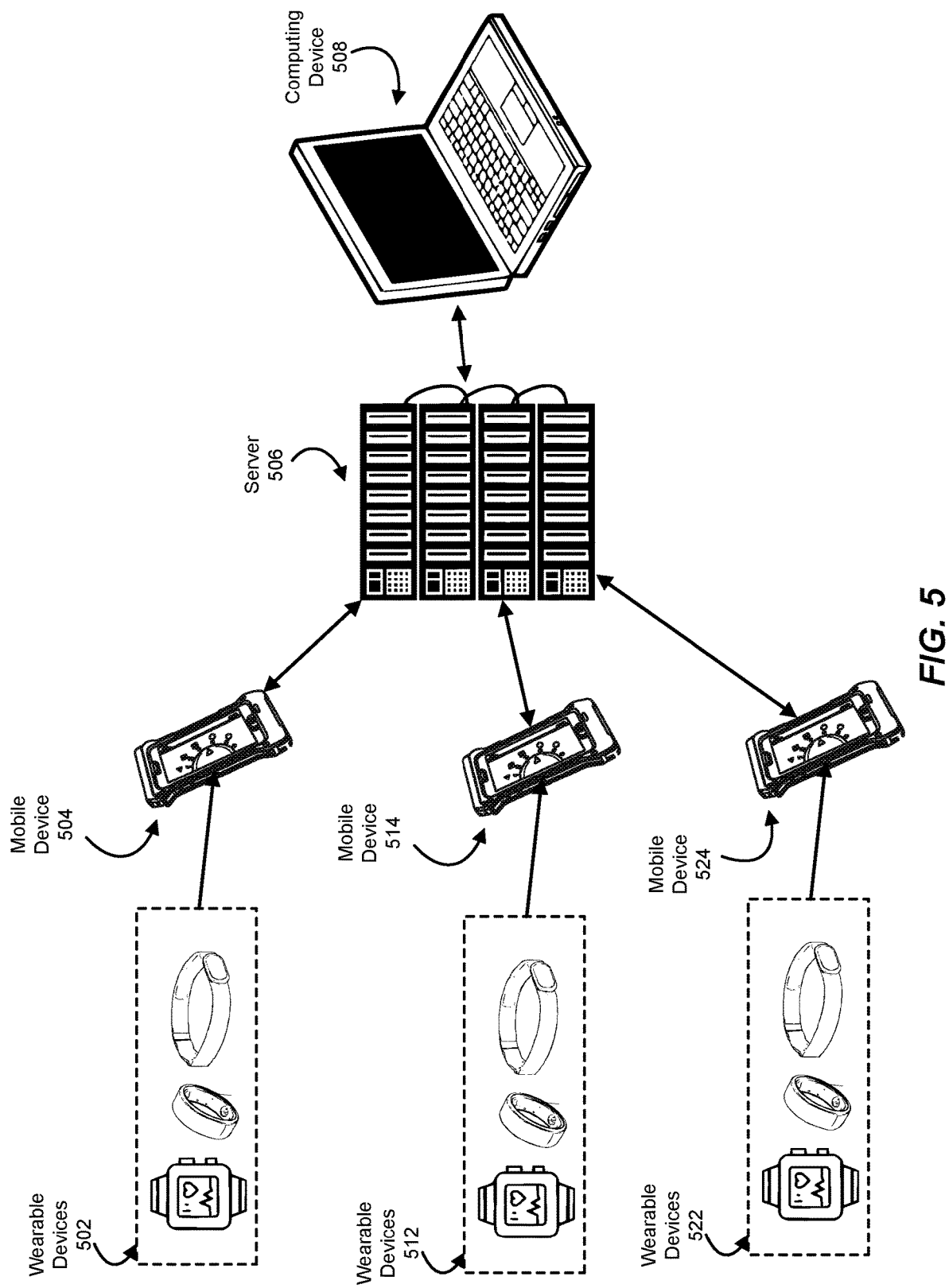
FIG. 5 is diagram of an example system for detecting early indications of illnesses and collecting other metrics about a team.

In some embodiments, a team leader may receive data from multiple sets of wearables worn by multiple members of a team. For example, as illustrated in FIG. 5, a set of wearable devices 502 worn by a first team member may send data to a mobile device 504 that then sends that data to a server 506. Similarly, a set of wearable devices 512 worn by a second team member may send data to a mobile device 514 that then sends that data to server 506 and/or a set of wearable devices 522 worn by a third team member may send data to a mobile device 524 that then sends that data to server 506. In one embodiment, server 506 may process the biomarker data for indications of illness and/or other information and may send the processed data and/or biomarker data to a computing device 508 operated by a team leader. Although illustrated as a single team of three members, in some embodiments, multiple teams of any number of members may send data to a server or servers to inform decision-making by a team leader.

In some embodiments, the systems described herein may analyze biomarker data for additional information beyond early indications of illness. For example, the systems described herein may analyze biomarker data for metrics that predict a team member's ability and/or readiness to complete a task. In one example, the systems described herein may analyze physiological data about a team member to determine a team member's ability to run, scale physical obstacles, and/or perform other physical tasks necessary to achieve a potential team goal. In some embodiments, wearables may collect data in addition to biomarkers, such as location (e.g., global positioning system coordinates) that may enable the collection of metrics such as the time it takes a team member to traverse a certain distance. In some examples, a team leader may use biomarker data and/or derived metrics to make determinations about whether to assign a team to accomplish a certain goal, assign a team to rest, assign a team to train, transfer team members between teams, and/or other relevant determinations.

In some examples, a team leader and/or other high-level decision-maker may use data provided by the systems described herein to allocate resources. In some embodiments, the systems described herein may prompt a team leader with resource allocation suggestions. For example, if one or more teams show early indications of an illness, the systems described herein may prompt a team leader to allocate additional resources (e.g., personal protective equipment, testing equipment, medical equipment, medical personnel, medicine, etc.) to the division and/or geographical area with the team in preparation for a potential outbreak of illness.

Figure 6:
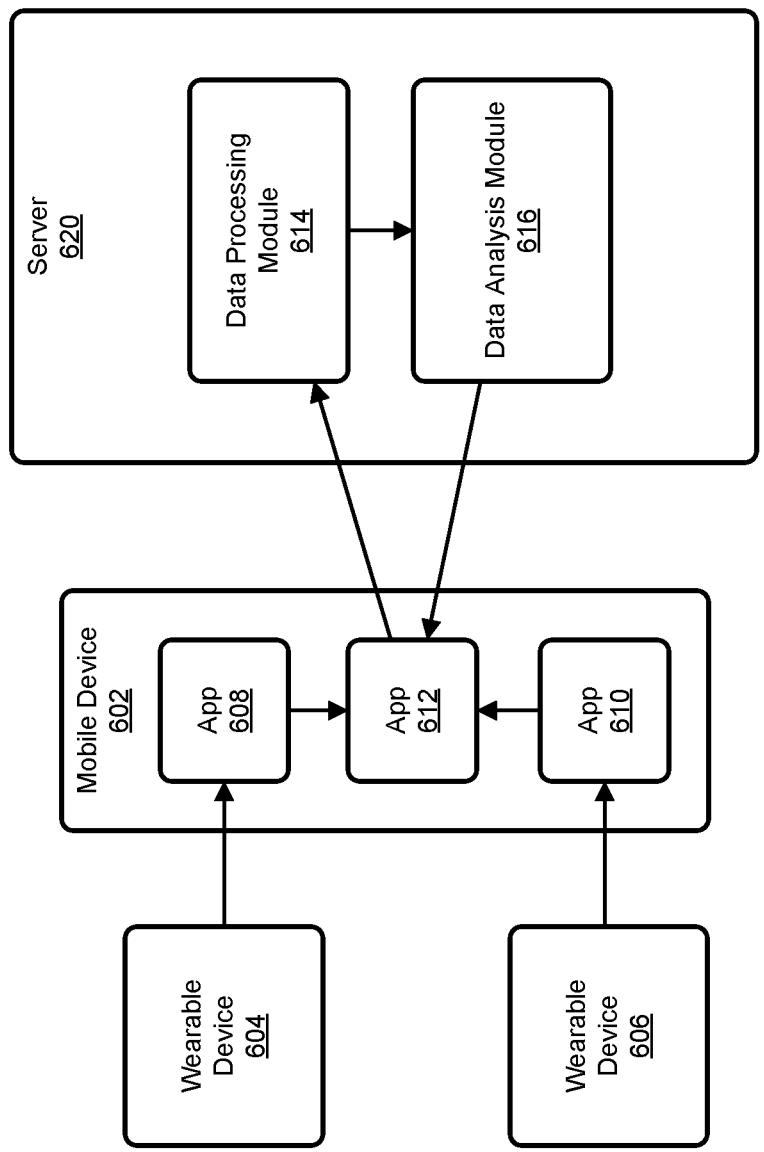
FIG. 6 is a block diagram of an example system for detecting early indications of illnesses.

In some embodiments, the systems described herein may include various software applications and/or modules. For example, as illustrated in FIG. 6, a wearable device 604 may send data to a device-specific app 608 and/or a wearable device 606 may send data to a device-specific app 610. In one embodiment, an app 612 may retrieve data from app 608 and/or app 610. In some embodiments, app 612 may retrieve data via an application programming interface (API). Additionally or alternatively, app 612 may intercept data sent to and/or received by app 608 and/or app 610. In one embodiment, app 612 may query a database to which app 608 and/or app 610 sends data rather than retrieving data directly from app 608 and/or app 610.

In some embodiments, app 612 may send data to a data processing module 614 hosted on a server 620. In one embodiment, data processing module 614 may remove any personally identifying information from the data. Additionally or alternatively, the systems described herein may remove personally identifying information before sending the data to server 620 (e.g., via app 612). In some embodiments, data processing module 614 may clean, format, and/or otherwise process data before sending the processed data to a data analysis module 616. In some examples, data processing module 614 may aggregate, regularize, and/or normalize data recorded by multiple different wearable devices that are each produced by a different third-party vendor and thus each format data in different ways.

In some embodiments, the systems described herein may compare (e.g., during an initial training phase) data gathered by commercial off-the-shelf wearable devices to clinical gold standards for data in order to account for variations in quality of data gathered by off-the-shelf wearable devices. In some embodiments, the fidelity of the diagnostic prediction and/or result may be dependent upon how much the data from the commercial sensors deviate from clinical gold standards. In some examples, if a suite of commercial wearable sensors are included as data source but clinical sensors are not available to be used to produce training data, the systems described herein may use the commercial sensors that are closest to the clinical gold standard to establish the algorithm baseline. In some embodiments, the systems described herein may derive diagnostic predictions and/or results from the rest of the sensors in the suite (e.g., the sensors farther from the clinical gold standard) with adjusted confidence values. For example, the systems described herein may rate wearable devices that gather lower quality data with lower confidence.

In one embodiment, data processing module 614 may perform outlier rejection, amplitude normalization, and/or bandpass filtering. In some embodiments, the systems described herein may use accelerometers as in indication for signal quality. In some examples, after the preprocessing step, the systems described herein may analyze metrics correlated to health conditions, such as the standard deviation of the normal to the normal interval for heart rate variability. In some embodiments, the systems described herein may combine heart rate data with accelerometer data to classify a user's activity level. In one embodiment, the systems described herein may aggregate and/or normalize data across time so that the combination of biomarkers from the various wearable devices are analyzed according to synchronized timelines.

In one embodiment, data analysis module 616 may analyze biomarker data collected by various wearable devices to detect early indications of illness. Although illustrated as a single server, server 620 may represent multiple physical and/or virtual servers in the same or different physical locations (e.g., cloud servers). Data analysis module 616 may perform a variety of types of analysis. For example, data analysis module 616 may apply one or more machine-learning techniques and/or classifiers, such as utilizing convolutional neural networks to perform the predictive analysis of biomarker data. In some examples, the systems described herein may generate a neural network with data sets that include wearable-based physiological data (e.g., heart rate variation features, temperature, etc.), activity features (e.g., sleep patterns, leisure, exercise, rigorous exercise, exercise recovery, etc.), socio-demographics (e.g., age, race, gender, etc.), medical history (e.g., pre-existing conditions such as hypertension, current medications, etc.), and/or physical conditions (e.g., body mass index, resting heart rate, blood pressure, oxygen saturation, etc.). In one embodiment, the data quality of the medical history and/or physical condition data may be marked manually and the systems described herein may weight the data according to the data quality markers.

In some embodiments, the systems described herein may train one or more machine learning models (e.g., neural networks) using general statistical methods. In one embodiment, the systems described herein may evaluate, at various sensitivity levels, the variables and the combinations of variables within the models for the specificity, accuracy, and positive predictive value for symptoms and diagnosis of a given illness (e.g., the seasonal flu, COVID-19, etc.). In some embodiments, the systems described herein may check this set of variables against the user's baseline physiological model as the systems described herein ingest new datasets in order to scan for deviations from norm. In one embodiment, the systems described herein may form a beta model with variables with the highest positive predictive values in a preset period of time before symptoms are observed and documented. In some examples, the beta models may then be formed into networks that represent the manifestation of the infection in each of the users. In one example, the systems described herein may then train the networked graphs of the models with collected data from the wearable devices to generate predictive diagnoses for the general population.

In some examples, the systems described herein may identify and/or track outbreaks of novel illnesses. For example, if the symptoms described herein detect a set of similar early indications of illness across multiple users and cannot match the set of early indications to a known illness, the systems described herein may transmit an alert (e.g., to a team leader or other high-level decision-maker with access to data from multiple users) that a potential novel illness has been detected. By tracking clusters of early indications in this way, the systems described herein may enable quick detection of novel illnesses and/or bioterror attacks. In some embodiments, the systems described herein may alert one or more predetermined organizations (e.g., a government agency tasked with public health) in response to detecting a possible outbreak of a novel illness.

In some embodiments, the systems described herein may track the transmission of an illness. For example, if the systems described herein detect an early indication of an illness in a user, the systems described herein may retrieve geolocation data for the user (e.g., from a location sensor such as a global positioning system sensor within a wearable device) and may identify other users who came in contact with the user recently (e.g., within the past two weeks). In some examples, the systems described herein may alert the additional users and/or one or more team leaders of the additional users about possible infection. Additionally or alternatively, the systems described herein may attempt to determine how and/or when the user was infected by analyzing data about potentially previously infected users with whom the user came into contact before displaying the early indication of the illness. In some embodiments, the systems described herein may perform contact tracing to warn potentially infected users who may have infected or been infected by a user who is displaying early indications of an illness.

Figure 7:
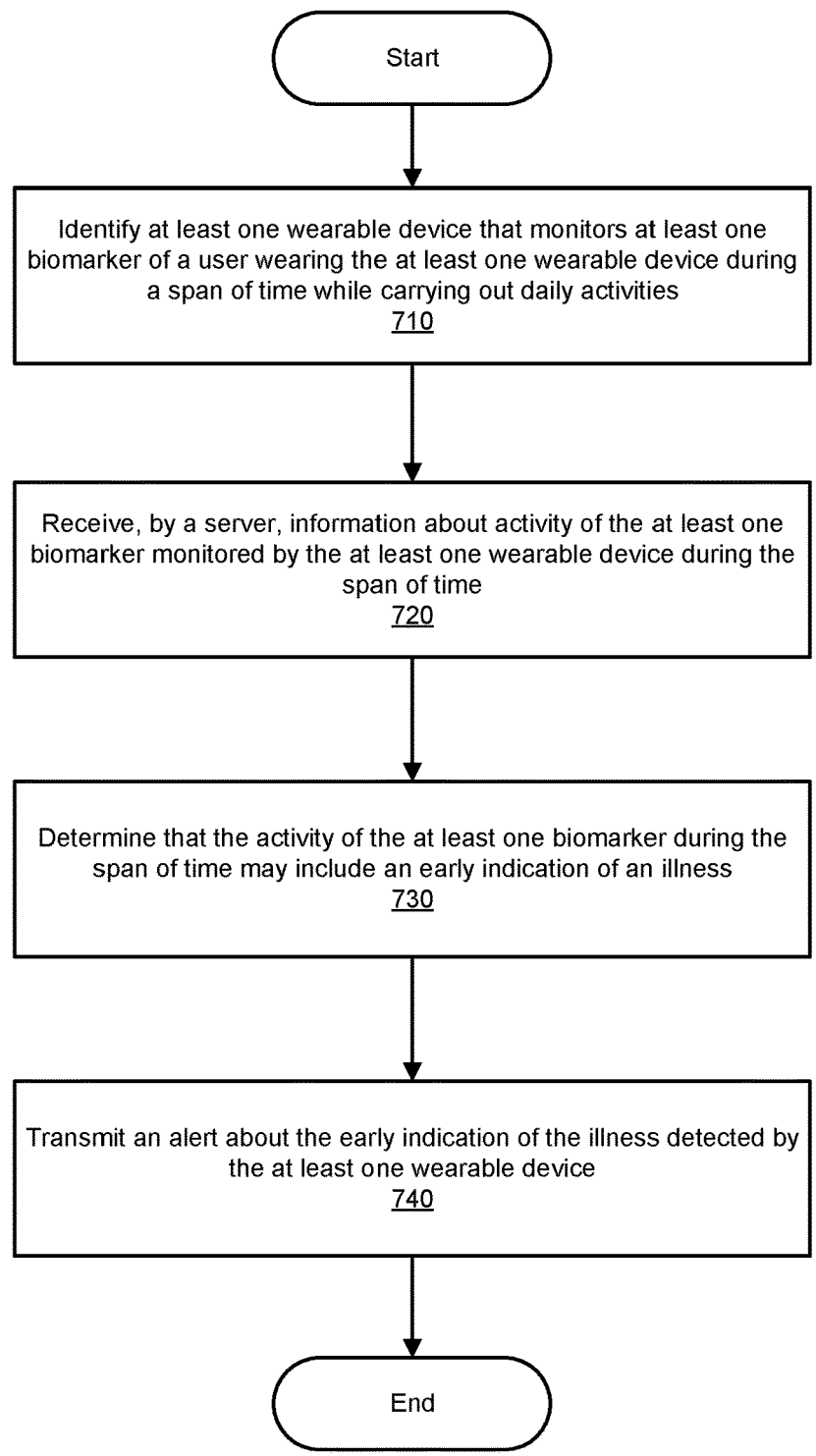
FIG. 7 is a flow diagram of an example method for detecting early indications of illnesses.

In some embodiments, the systems described herein may perform a series of steps to identify early indications of illness. As illustrated in FIG. 7, at step 710, one or more of the systems described herein may identify at least one wearable device that monitors at least one biomarker of a user wearing the at least one wearable device during a span of time while carrying out daily activities.

In one embodiment, the systems described herein may identify the at least one wearable device by identifying an application to which the wearable device transmits data, and interfacing with the application to receive the data. In one example, the wearable device may include a third-party exercise monitor. In one embodiment, the biomarker may include at least one of heart rate variability, heart rate, breathing rate, temperature, and/or sleep disruption.

At step 720, one or more of the systems described herein may receive, by a server, information about activity of the at least one biomarker monitored by the at least one wearable device during the span of time.

At step 730, one or more of the systems described herein may determine that the activity of the at least one biomarker during the span of time includes an early indication of an illness.

In some embodiments, the systems described herein may determine that the activity of the at least one biomarker during the span of time includes the early indication the illness by correlating the activity of multiple biomarkers received from a plurality of wearable devices. In some examples, the systems described herein may determine that the activity of the at least one biomarker during the span of time includes the early indication of the illness by comparing the activity of the at least one biomarker during the span of time to baseline activity data previously recorded for the user by the at least one wearable device.

In some examples, the systems described herein may determine that the activity of the at least one biomarker during the span of time includes the early indication of the illness by receiving a selection of a specific illness from a list of illnesses with known indications and analyzing the activity of the at least one biomarker for at least one indication of the specific illness. In some examples, the systems described herein may receive the selection of the specific illness from the list of illnesses by receiving a selection of the illness from a team leader of a team that includes the user.

At step 740, one or more of the systems described herein may transmit an alert about the early indication of the illness detected by the at least one wearable device.

In some examples, the systems described herein may transmit the alert by transmitting the alert to the user. In some examples, the systems described herein may transmit the alert by transmitting the alert to a team leader of a team by the user.

In one embodiment, systems described herein may, in response to determining that the activity of the at least one biomarker during the span of time includes the early indication of the illness, (i) retrieve location data from the location sensor of the wearable device, (ii) identify, based on the location data, at least one additional user that came into proximity to the user of the wearable device during the span of time, and (iii) transmit an additional alert in response to identifying the at least one additional user that came into proximity to the user of the wearable device during the span of time.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A computer-implemented method comprising:
   identifying a user and at least one additional user as both being registered as belonging to a team;
   identifying at least one wearable device configured to monitor at least one biomarker of a user wearing the at least one wearable device during a span of time while carrying out daily activities;
   receiving, from the at least one wearable device, information about activity of the at least one biomarker at two or more different points of time during the span of time;
   analyzing the information about the activity of the at least one biomarker for an indication of an infectious disease; and
   transmitting, in response to identifying the indication of the infectious disease of the user and to determining that both the user and the at least one additional user are registered as belonging to the team, an alert that is informative about a potential infection to the at least one additional user.

2. The computer-implemented method of claim 1, wherein transmitting the alert comprises transmitting the alert to the user.

3. The computer-implemented method of claim 1, wherein transmitting the alert comprises transmitting the alert to a device associated with a team leader account of a team comprising the user.

4. The computer-implemented method of claim 1, wherein analyzing the activity of the at least one biomarker for the indication of the infectious disease comprises:
   selecting the infectious disease from a list of illnesses with known indications and
   analyzing the activity of the at least one biomarker for at least one indication of the infectious disease.

5. The computer-implemented method of claim 4, wherein selecting the specific infectious disease from the list of illnesses comprises receiving a selection of the infectious from a team leader of the team.

6. The computer-implemented method of claim 1, wherein analyzing the information about the activity of the biomarker comprises comparing the activity of the at least one biomarker during the span of time to baseline activity data previously recorded for the user by the at least one wearable device.

7. The computer-implemented method of claim 1, further comprising:
   identifying an application to which the at least one wearable device transmits data and
   interfacing with the application to receive the data.

8. The computer-implemented method of claim 1, wherein the biomarker comprises:
   a heart rate variability.

9. The computer-implemented method of claim 1, wherein analyzing the information about the activity of the at least one biomarker comprises detecting an inflammatory response based at least on part on at least one of:
   heart rate; and
   heart rate variability.

10. The computer-implemented method of claim 1:
    wherein the wearable device comprises a location sensor;
    further comprising, in response to the indication of the infectious disease:
       retrieving location data from the location sensor of the wearable device;
       determining, based on the location data, a proximity of the at least one additional user to the user of the wearable device during the span of time; and
       transmitting an additional alert in response to determining the proximity of the at least one additional user to the user.

11. The computer-implemented method of claim 1, wherein analyzing the information about the activity of the at least one biomarker comprises correlating activity of multiple biomarkers received from a plurality of separate wearable devices worn by the user, each separate wearable device within the plurality of separate wearable devices being produced by a different third-party vendor.

12. The computer-implemented method of claim 1, wherein the daily activities comprise at least two of:
   performing job functions;
   exercising; and
   sleeping.

13. The computer-implemented method of claim 1, further comprising analyzing, by the computing system, a readiness of the user to perform a specified task based at least in part on the activity of the at least one biomarker during the span of time.

14. The computer-implemented method of claim 1, wherein analyzing the information about the activity of the at least one biomarker comprises analyzing the activity of the at least one biomarker via a machine-learning classifier.

15. The computer-implemented method of claim 14, wherein the machine-learning classifier comprises a convolutional neural network.

16. The computer-implemented method of claim 1, wherein the wearable device comprises at least one of:
   a watch;
   a chest strap; and
   a ring.

17. A system comprising:
   a non-transitory memory; and
   one or more hardware processors configured to execute instructions from the non-transitory memory, the instructions configured to cause the processor to perform operations comprising:
      identifying a user and at least one additional user as both being registered as belonging to a team;
      identifying at least one wearable device configured to monitor at least one biomarker of a user wearing the at least one wearable device during a span of time while carrying out daily activities;
      receiving, from the at least one wearable device, information about activity of the at least one biomarker at two or more different points of time during the span of time;
      analyzing the information about the activity of the at least one biomarker for an indication of an infectious disease; and
      transmitting, in response to identifying the indication of the infectious disease of the user and to determining that both the user and the at least one additional user are registered as belonging to the team, an alert that is informative about a potential infection to the at least one additional user.

18. The system of claim 17, wherein analyzing the information about the activity of the at least one biomarker comprises detecting an inflammatory response based at least on part on at least one of:
   heart rate; and
   heart rate variability.

19. A system comprising:
   at least one wearable device configured to monitor at least one biomarker of a user wearing the at least one wearable device during a span of time while carrying out daily activities;
   a non-transitory memory; and
   one or more hardware processors configured to execute instructions from the non-transitory memory, the instructions configured to cause the processor to perform operations comprising:
      identifying a user and at least one additional user as both being registered as belonging to a team;
      receiving, from the at least one wearable device, information about activity of the at least one biomarker at two or more different points of time during the span of time;
      analyzing the information about the activity of the at least one biomarker for an indication of an infectious disease; and
      transmitting, in response to identifying the indication of the infectious disease and to determining that both the user and the at least one additional user are registered as belonging to the team, an alert that is informative about a potential infection to the at least one additional user.

20. The system of claim 19, wherein analyzing the information about the activity of the at least one biomarker comprises detecting an inflammatory response based at least on part on at least one of:
   heart rate; and
   heart rate variability.

* * * * *